United States Patent [19]

Sasaki et al.

[11] Patent Number: 5,059,573
[45] Date of Patent: Oct. 22, 1991

[54] PROCESS FOR PRODUCING MOLYBDENUM-CONTAINING METAL OXIDE FLUID-BED CATALYST

[75] Inventors: Yutaka Sasaki; Kunio Mori; Kiyoshi Moriya, all of Kanagawa, Japan

[73] Assignee: Nitto Chemical Industry Co., Ltd., Tokyo, Japan

[21] Appl. No.: 480,698

[22] Filed: Feb. 15, 1990

[30] Foreign Application Priority Data

Feb. 16, 1989 [JP] Japan .................................. 1-35124

[51] Int. Cl.$^5$ ...................... B01J 23/16; B01J 21/00; B01J 27/057; B01J 27/18
[52] U.S. Cl. .................................. 502/205; 502/206; 502/209; 502/211; 502/215; 502/246; 502/249; 502/255
[58] Field of Search ............... 502/255, 246, 205, 206, 502/209, 211, 215, 212

[56] References Cited

U.S. PATENT DOCUMENTS

| | | | |
|---|---|---|---|
| 2,889,287 | 6/1959 | Scott, Jr. | 502/255 |
| 3,975,302 | 8/1976 | Courty et al. | 502/255 |
| 3,984,477 | 10/1976 | Kubo et al. | |
| 4,181,629 | 1/1980 | Cairati et al. | 502/255 |
| 4,354,044 | 10/1982 | Aoshima et al. | |
| 4,418,007 | 11/1983 | Derrien . | |

FOREIGN PATENT DOCUMENTS

0181035 5/1986 European Pat. Off. .
2080231 11/1971 France .
1217649 12/1970 United Kingdom .

Primary Examiner—Carl F. Dees
Attorney, Agent, or Firm—Sughrue, Mion, Zinn, Macpeak & Seas

[57] ABSTRACT

A process for producing a molybdenum-containing metal oxide fluid-bed catalyst comprising, as essential components, (i) at least one element selected from the group consisting of iron, bismuth, and tellurium,
(ii) molybdenum, and
(iii) silica, which comprises (a) adjusting an aqueous slurry containing a raw material providing element (i), a molybdenum compound, a silica sol, and a chelating agent capable of inhibiting gelation of the slurry of a pH of at least 6, or (b) adjusting an aqueous slurry containing a raw material providing element (i), a molybdenum compound and a chelating agent capable of inhibiting gelation to a pH of at least 6 and mixing the slurry with a silica sol, then spray drying the thus pH-adjusted aqueous slurry, and calcining the resulting particles.

8 Claims, No Drawings

PROCESS FOR PRODUCING MOLYBDENUM-CONTAINING METAL OXIDE FLUID-BED CATALYST

FIELD OF THE INVENTION

This invention relates to a process for producing a molybdenum-containing metal oxide fluid-bed catalyst suitable for gaseous phase oxidation reactions of organic compounds. More particularly, it relates to a process for producing a molybdenum-containing metal oxide fluid-bed catalyst comprising, as essential components, (i) at least one element selected from the group consisting of iron, bismuth and tellurium, (ii) molybdenum, and (iii) silica. Oxidation reactions of organic compounds herein referred to include an oxidation reaction, an oxidative dehydrogenation reaction and an ammoxidation reaction.

BACKGROUND OF THE INVENTION

A number of molybdenum-based catalysts for oxidation reactions of organic compounds are known. Examples of such catalysts include P.Mo.Bi catalysts as disclosed in JP-B-36-3563 (corresponding to U.S. Pat. No. 2,941,007) and JP-B-36-5870 (corresponding to U.S. Pat. No. 2,904,580) (the term "JP-B" as used herein means an "examined published Japanese patent application"); P.Mo.Fe.Bi catalysts as disclosed in JP-B-38-17967 (corresponding to U.S. Pat. No. 3,226,422) and JP-B-39-3670 (corresponding to U.S. Pat. No. 3,171,859); Mo.Te catalysts as disclosed in JP-B-37-11008; Mo.Bi.Sb catalysts as disclosed in JP-B-39-10111; Mo.Bi.Pb catalysts as disclosed in JP-B-42-7774; and Mo.Bi.Cr catalysts as disclosed in JP-A-50-64191 (corresponding to U.S. Pat. No. 4,174,354) (the term "JP-A" as used herein means an "unexamined published Japanese patent application"). Further, several improvements have been proposed with respect to catalyst activity as disclosed, e.g., in JP-B-47-27490 (corresponding to U.S. Pat. No. 3,959,384), JP-B-54-22795 (corresponding to U.S. Pat. No. 3,984,477), and JP-B-60-36812 (corresponding to U.S. Pat. Nos. 4,600,541 and 4,377,534).

Many of these catalysts have disadvantages such as low catalytic activity and strength when applied to a fluidized bed reaction. Hence, various proposals have been made on a process for producing the catalyst. For example, JP-B-37-8568 (corresponding to U.S. Pat. No. 3,044,965) discloses a method of adding at least 1% by weight of ammonium nitrate to a slurry containing catalyst components; JP-B-57-49253 (corresponding to U.S. Pat. No. 3,746,657) discloses a method of adding a silica sol stepwise to a molybdenum aqueous solution at a temperature of not higher than 66° C.; JP-A-56-44046 (corresponding to U.S. Pat. Nos. 4,453,006 and 4,280,929) discloses a method of using fumed silica; JP-B-54-12913 discloses a method of preparing a molybdenum-bismuth-iron-sodium-phosphorus catalyst within a limited narrow rang of composition; JP-A-57-65329 (U.S. Pat. No. 3,872,148) discloses a method for preparing an attritionresistant molybdenum-bismuth-antimony fluid-bed catalyst which comprises spray drying a catalyst component-containing slurry having a pH of 1 or less and a temperature of 60° C. or lower; JP-A-53-10388 discloses a method comprising mixing a molybdic acid aqueous solution with a solid bismuth compound and adjusting the pH of the slurry to 8 to 10; and JP-B-59-51848 (corresponding to U.S. Pat. No. 4,418,007) discloses a method comprising simultaneously adding a bismuth salt aqueous solution and aqueous ammonia to a molybdic acid aqueous solution having a pH of from 6 to 8.

However, the so far proposed processes for producing a catalyst are not always satisfactory in achieving both catalytic activity and strength. In particular, the conventional processes for producing a molybdenum-containing catalyst give rise to various problems when applied to the production of molybdenum-based catalysts as desired in the present invention. For example, the catalyst prepared according to the process of JP-B-54-22795 (corresponding to U.S. Pat. No. 3,984,477) failed to achieve satisfactory reaction results as showing only a low acrylonitrile yield and a higher ammonia combustion as proved in Comparative Examples 5 and 6 hereinafter described. Further, where a mixture of catalyst raw materials is merely adjusted to a pH between 8 and 10, gelation of a silica sol proceeded to increase the viscosity of the slurry so that the slurry cannot be sufficiently spraydried as demonstrated in Comparative Examples 1 to 3 hereinafter described. In this case, also, satisfactory results cannot be obtained with respect to physical properties of the catalyst, particularly strength.

SUMMARY OF THE INVENTION

An object of this invention is to provide a process for producing a molybdenum-containing metal oxide fluid-bed catalyst having satisfactory physical properties, such as strength, and high activity such that a desired oxidation product can be provided in a high yield.

As a result of extensive investigations, it has now been found that the above object of this invention is accomplished by use of a chelating agent having a function of inhibiting gelation of a silica sol in combination with pH adjustment of a catalyst component-containing slurry.

The present invention provides a process for producing a molybdenum-containing metal oxide fluid-bed catalyst comprising, as essential components, (i) at least one element selected from the group consisting of iron, bismuth, and tellurium,
(ii) molybdenum, and
(iii) silica, which comprises (a) adjusting an aqueous slurry containing a raw material providing element (i), a molybdenum compound, a silica sol, and a chelating agent capable of inhibiting gelation to a pH of at least 6, or (b) adjusting an aqueous slurry containing a raw material providing element (i), a molybdenum compound and a chelating agent capable of inhibiting gelation to a pH of at least 6 and mixing the slurry with a silica sol, then spray drying the thus pH-adjusted aqueous slurry, and calcining the resulting particles.

DETAILED DESCRIPTION OF THE INVENTION

Depending on the kinds and amounts of optional components used in combination with the above-described essential components, the catalyst prepared by the process of this invention can be generally represented by empirical formula:

wherein

C represents at least one element selected from the group consisting of Fe, Bi, and Te;

D represents at least one element selected from the group consisting of Ni, Co, Mg, Cr, Mn, Cu, Zn, Ga, Ge, Cd, In, Sn, Sb, V, W, Re, Pb, Ru, Rh, Pd, Os, Ir, Pt, Th, U, La, Ce, Pr, Nd, Sm, Eu, Gd, Al, Ti, Ta, Nb, and Zr, preferably Ni, Co, Mg, Cr, Mn, Cu, Zn, Ga, Ge, In, Sn, Sb, V, W, Pd, Pt, U, La, Ce, Al, Ti, Ta, Nb and Zr;

E represents at least one element selected from the group consisting of P and B;

F represents at least one element selected from the group consisting of Li, Na, K, Rb, Cs, Ca, Sr, Ba, and Tl, preferably Li, Na, K, Rb and Cs;

O is oxygen; and a, b, c, d, e, f, g, and h each represents an atomic ratio, wherein when $a=8$ to 12,
$c=0.5$ to 20 (preferably 0.5 to 15),
$d=0$ to 25 (preferably 0 to 23),
$e=0$ to 5 (preferably 0 to 3),
$f=0$ to 5 (preferably 0 to 3),
g is a number decided by a, b, c, d, e, and f so as to form an oxide of the corresponding elements, and
$h=20$ to 150 (preferably 30 to 120).

The optional components other than molybdenum, component C, and silica can appropriately be selected so as to control the selectivity of the desired reaction product, the reaction rate, catalyst physical properties, and the like.

Raw materials for the components forming the catalyst can be selected from various compounds of the respective elements involved, such as the oxides, the hydroxides, the chlorides, and the nitrates.

Examples of suitable raw materials for the molybdenum component include molybdenum oxides, e.g., molybdenum trioxide, molybdic acid, molybdic acid salts, e.g., ammonium paramolybdate and ammonium metamolybdate, heteropoly-acids, e.g., phosphomolybdic acid and silicomolybdic acid, and heteropoly-acid salts.

Raw materials for the iron component include ferrous oxide, ferric oxide, ferrosoferric oxide, iron nitrate, iron chloride, and iron hydroxide. Metallic iron dissolved in heated nitric acid can also be employed.

Raw materials for the bismuth component include bismuth salts, e.g., bismuth nitrate and bismuth sulfate, bismuth trioxide, and a metallic bismuth oxidation product with nitric acid.

Raw materials for the tellurium component include telluric acid, tellurous acid, tellurium dioxide, tellurium trioxide, and metallic tellurium dissolved in nitric acid.

Where optional elements represented by D, E, and F in the above empirical formula are present in the catalyst, these elements can be used in the form of the oxides, the hydroxides, the chlorides, the nitrates and the like.

The chelating agent which is used in the present invention possesses the function of inhibiting gelation. Examples of suitable chelating agents which can be used include amines, e.g., ethylenediamine, trimethylenediamine, tetraethylenediamine, N,N'-dimethylethylenediamine, triethanolamine, pyridine, and bipyridyl; aminopolycarboxylic acids, e.g., ethylenediaminediacetic acid, ethylenediaminetetraacetic acid, and nitrilotriacetic acid; polycarboxylic acids, e.g., oxalic acid, malonic acid, succinic acid, glutaric acid, maleic acid, fumaric acid, citraconic acid, itaconic acid, adipic acid, diglycolic acid, tricarballylic acid, and propane-1,1,2,3-tetracarboxylic acid; aromatic carboxylic acids, e.g., phthalic acid, mandelic acid, sulfosalicylic acid, and benzoic acid; hydroxycarboxylic acids and keto-carboxylic acids, e.g., glycolic acid, lactic acid, hydroxypropionic acid, malic acid, tartaric acid, citric acid, isocitric acid, gluconic acid, ascorbic acid, pyruvic acid, oxalacetic acid, and diglycolic acid; thiols and sulfur compounds, e.g., thioglycolic acid, thiodiglycolic acid, and mercaptopropanol; amino acids, e.g., glycine, alanine, asparagine, glutamic acid, methionine, and phenylalanine; diketones, e.g., acetylacetone, acetonylacetone, and benzoylacetone; phosphonic acids, e.g., phosphonopropane-1,2,3-tricarboxylic acid and phosphonomethyliminodiacetic acid; and chelated compounds formed by these chelating agents and a catalyst forming element, preferably ethylenediamie, trimethylenediamine, triethanolamine, and pyridine; ethylenediaminediacetic acid, ethylenediaminetetraacetic acid and nitrilotriacetic acid; oxalic acid, malonic acid, succinic acid, glutaric acid, maleic acid, and fumaric acid; glycolic acid, lactic acid, hydroxypropionic acid, malic acid, tartaric acid, citric acid, isocitric acid, gluconic acid, and ascorbic acid; thioglycolic acid and thiodiglycolic acid; glycine, alanine, asparagine, and glutamic acid; acetylacetone, and acetonylacetone; and phosphonopropane-1,2,3-tricarboxylicacid.

These chelating agents may be used either individually or as a combination of two or more thereof. The chelating agent to be used is preferably water soluble.

According to the present invention, the catalyst is obtained by adjusting an aqueous slurry containing the raw material for the catalyst component (i), e.g., iron, a molybdenum compound, a silica sol, and a chelating agent capable of inhibiting gelation to a pH of 6 or higher, or adjusting an aqueous slurry containing the above-described components other than the silica sol to a pH of 6 or higher and then mixing the slurry with a silica sol; spray drying the slurry; and then calcining the resulting fine particles.

From the viewpoint of ease of industrial operation, the slurry is usually adjusted to a pH of from 6 to 11, and preferably from 6 to 10.5. As the material for adjusting a pH of the slurry, amines, for example, ammonia, methyl amine or their aqueous solution, etc. can be used.

It is not clear why the use of the chelating agent and the pH adjustment induce any reaction in the slurry to contribute to the performance properties of the catalyst. However, if the pH of the slurry is not adjusted to 6 or higher, the catalyst ultimately obtained has deteriorated properties, particularly yield of the desired reaction product as shown in Comparative Examples 5 and 6 hereinafter described. And, when such a catalyst is used in ammoxidation, the ammonia combustion is higher.

On the other hand, if the catalyst is prepared by a pH adjustment to 6 or more without using the chelating agent, the viscosity of the slurry increases over 2,000 centipoises, which make it difficult to stir and spray the slurry in the spray drying, and the thus prepared catalyst has reduced strength, thus giving lower attrition resistance as shown in Comparative Examples 1 and 2. To the contrary, where the chelating agent is present in the slurry, the slurry has a relatively low viscosity even at a pH of 6 or higher and exhibits stable properties. Thus, a high strength catalyst as demonstrated in Examples hereinafter described, is obtained.

The amount of the chelating agent to be added preferably ranges from 0.1 to 10% by weight, more preferably from 0.5 to 8% by weight, based on the weight of the oxide catalyst ultimately obtained. If the amount is less than 0.1% by weight, the effect of improving catalyst strength is small, and if the amount exceeds 10% by weight, the resulting catalyst sometimes cracks.

As stated above, while the mechanism of the effects produced by addition of the chelating agent is not clear, what is important is that gelation of the slurry is inhibited. While not desiring to be found, it may well be that the chelating agent serves as a metallic ion masking agent to inhibit metallic ions from neutralizing the charges of the silica sol particles.

To stabilize the slurry properties and to further improve performance properties of the catalyst ultimately obtained, it is desirable, though not essential, to subject the slurry after pH adjustment and before spray drying to a heat treatment at a temperature of from 50 to 120° C. while maintaining the catalyst in a slurry form. In this case, the heat treatment is suitably carried out at the above recited temperature for at least 10 minutes. When the slurry having a pH of less than 6 is heat treated and further processed without pH adjustment to 6 or more, the resulting catalyst has reduced yield of the desied reaction product as shown in Comparative Example 6 hereinafter described, particularly accompanied with the high ammonia combustion in ammoxidation reaction.

Where a catalyst slurry having a pH of 6 or higher is heat treated under the above-described conditions prior to spray drying, the slurry after the heat treatment may have a pH of 6 or less.

The thus prepared slurry is then spray dried to obtain fine spherical particles. Spray drying can be carried out in a usual manner using a pressure nozzle type spray drier, a rotary disc type spray drier, etc. as shown in *Chemical Engineer's Handbook*, 5th Edit., pp. 20-58, Perry, R. H. and Chilton, C. McGraw-Hill (1973). The slurry to be spray dried preferably has a concentration of from about 10 to about 40% by weight, calculated as the oxides of constituent elements. The slurry concentration and spray drying conditions are appropriately selected so as to obtain particles having a desired particle size distribution.

If desired, the fine particles obtained by spray drying may be subjected to a further drying treatment. Finally, the particles are calcined at a temperature of from about 500° C. to about 750° C. for a period of from about 1 to about 50 hours to thereby provide the catalyst with the desired activity and physical properties. Calcining may be effected at a fixed temperature or an elevated temperature to conduct a pre-calcination followed by final calcination. The precalcination is preferably carried out at a temperature of from about 200° C. to about 500° C. for a period of from about 1 to about 50 hours. The calcining is preferably performed in a non-reductive atmosphere and, more preferably from the economical standpoint, in an air stream. Many types of calcining devices, e.g., a tunnel furnace, a rotary kiln, a fluidized-bed calciner, etc., can be used.

The catalyst according to the present invention is useful for oxidation reactions of organic compounds, including oxidation, oxidative dehydrogenation, and ammoxidation.

Organic compounds which can be subjected to oxidation reactions using the catalyst of the invention include propylene, isobutene, methanol, ethanol, t-butanol, methyl tbutyl ether, etc., and the corresponding aldehydes, nitriles, conjugated dienes, etc. in high yields are obtained from these organic compounds. Particularly satisfactory results can be obtained when the catalyst is applied to an oxidation reaction of propylene, isobutene, or t-butanol.

The catalyst prepared by the process of this invention produces particularly noticeable effects when applied to oxidation reactions, and especially ammoxidation of organic compounds to achieve high yields of the desired products while inhibiting the combustion of ammonia.

According to the present invention, a molybdenum-containing metal oxide fluid-bed catalyst for oxidation which exhibits high activity with reduced attrition loss can be obtained through simple and easy operation of the addition of a chelating agent and pH adjustment. Moreover, since the catalyst prepared causes ammonia combustion to a lesser extent, it is markedly effective as a catalyst for ammoxidation to attain a high product yield and to be able to decrease ratio of ammonia to organic compound.

The present invention is now illustrated in greater detail by reference to the following Examples, but it should be understood that the present invention is not deemed to be limited thereto. All the percents are given on a weight basis unless otherwise specified. In the Examples and Comparative Examples, the strength and activity of the catalyst were evaluated in accordance with the following test methods.

Attrition Testing

Atfrition testing carried out according to the method described in *Test Method For Synthetic Cracking Catalysts*, 6/31-4m-1/57, American Cyanamid Co., which is known as a test method for catalysts for fluid catalytic cracking process. Attrition loss (%) was calculated from the following relationship:

Attrition Loss (%): $R = B \times 100/(C-A)$ wherein A is the weight loss of the catalyst on attrition within the first 5 hours; B is the weight loss of the catalyst after 5 hours of attrition up to 25 hours of attrition; and C is the weight of a catalyst being tested [C=50 (g) in this test].

The higher the attrition resistance of the catalyst, the smaller the attrition loss (R value).

Activity Testing:

The activity of the fluid-bed catalyst was tested using ammoxidation of propylene as a representative reaction as follows.

The catalyst tested was charged in a fluidized bed reactor having an inner diameter of 25 mm and a height of 40 cm so as to have a prescribed contact time and maintained at a reaction temperature of 410° C. A mixed gas of propylene, ammonia, and oxygen at a molar ratio of 1:1.2:1.95 and air was fed to the reactor at a feed rate of 6.5 l per hour (NTP) conversion). The reaction pressure was atmospheric pressure.

The yield of ammoxidation product (acrylonitrile), the conversion of starting organic compound (propylene), and the ammonia combustion were calculated using the relationships shown below.

Acrylonitrile Yield (%) =

-continued

Propylene Conversion (%) =
$$\frac{\text{Weight of Carbon in Acrylonitrile Produced}}{\text{Weight of Carbon in Propylene Fed}} \times 100$$

$$\frac{\text{Weight of Carbon in Propylene Consumed}}{\text{Weight of Carbon in Propylene Fed}} \times 100$$

Ammonia Combussion (%) =

$$\frac{\text{(Weight of Nitrogen in Ammonia Fed)} - \text{(Weight of Nitrogen in Unreacted Ammonia)} - \text{(Weight of Nitrogen in Collected Nitrogen—Containing Organic Compound)}}{\text{Weight of Nitrogen in Ammonia Fed}} \times 100$$

EXAMPLE 1

A catalyst having the empirical formula $Mo_{10}Bi_{1.0}Fe_{2.0}Ni_{6.5}Sb_{15}P_{0.2}K_{0.4}O_{71.7}(SiO_2)_{60}$ was prepared as follows.

In 20 ml of water was dissolved 3.92 g of potassium nitrate, and the solution was added to 1745 g of a 20% silica sol. A solution of 171.0 g of ammonium paramolybdate in 510 ml of water was added to the above mixture with stirring. Subsequently, a solution of 225.6 g of antimony tetroxide powder and 186.8 g of nickel nitrate in 190 ml of water, a solution of 79.8 g of iron nitrate in 80 ml of water, a solution of 47.9 g of bismuth nitrate in 48 ml of 10% nitric acid, and 2.23 g of a 85% phosphoric acid aqueous solution were successively added thereto to prepare a slurry. The resulting slurry had a pH of 1 or less. To the slurry was added 40 g of ethylenediamine, which amount corresponded to 5% of the oxide catalyst, and dissolved therein. A 15% ammonia aqueous solution was added to the slurry with stirring to adjust the slurry to a pH of 8.

The slurry was spray dried in a rotary disc type spray drier with the inlet temperature and the outlet temperature being controlled at 320° C. and 160° C., respectively. The resulting fine particles were heated at 250° C., then calcined at 400° C. for 2.5 hours, and finally calcined at 620° C. for 3 hours.

The thus prepared catalyst was charged in a fluidized bed reactor so as to have a contact time of 4 seconds, and ammoxidation of propylene was performed at a reaction temperature of 410° C. The acrylonitrile yield was 86.1%; the propylene conversion was 98.7%, the ammonia combustion was 16%, and the R value was 1.2.

EXAMPLES 2 AND 3

A catalyst having the same composition as in Example 1 was prepared in the same manner as in Example 1, except that 40 g of triethanolamine or ethylenediaminetetraacetic acid was dissolved in the slurry in place of ethylenediamine as used in Example 1, which amount corresponded to 5% of the oxide catalyst, and the pH of the slurry was adjusted to a pH of 6 or 0, respectively.

EXAMPLE 4

A catalyst having the empirical formula $Mo_{10}Bi_{1.5}Fe_{2.0}Ni_{6.0}Sb_{10}K_{0.2}O_{61.35}(SiO_2)_{60}$ was prepared as follows.

In 20 ml of water was dissolved 2.14 g of potassium nitrate, and the solution was added to 1910 g of a 20% silica sol. To the mixture was added a solution of 187.1 g of ammonium paramolybdate in 560 ml of water with stirring. Subsequently, a solution of 164.6 g of antimony tetroxide powder and 188.7 g of nickel nitrate in 190 ml of water, a solution of 87.4 g of iron nitrate in 88 ml of water, and a solution of 78.7 g of bismuth nitrate in 80 ml of 10% nitric acid were successively added thereto to prepare a slurry. In the slurry was dissolved 40 g (corresponding to 5% of the oxide catalyst) of tartaric acid. A 15% ammonia aqueous solution was then added to the slurry with stirring to adjust the slurry to a pH of 8. The slurry was subjected to a heat treatment at 100° C. for 2 hours under refluxing. The slurry was then spray dried and calcined in the same manner as in Example 1.

EXAMPLE 5

A catalyst having the same composition as in Example 4 was prepared in the same manner as in Example 4, except that 955 g out of the 20% silica sol was added at the time of mixing the catalyst raw materials, the amount of tartaric acid added to the slurry was changed to 20 g which corresponded to 2.5% of the oxide catalyst, and the rest of the silica sol (i.e., 955 g) was added after the heat treatment.

EXAMPLE 6

A catalyst having the same composition as in Example 5 was prepared in the same manner as in Example 5, except for changing the amount of tartaric acid added to the slurry to 8 g which corresponded to 1% of the oxide catalyst and adding the total amount of the 20% silica sol after the heat treatment.

EXAMPLES 7 TO 9

A catalyst having the same composition as in Example 4 was prepared in the same manner as in Example 4, except that 40 g (corresponding to 5% of the oxide catalyst) of gluconic acid, citric acid, or nitrilotriacetic acid was dissolved in the slurry in place of tartaric acid and the pH of the slurry was adjusted to a pH of 6, 9.5, or 11, respectively.

EXAMPLE 10

A catalyst having the empirical formula $Mo_{10}Bi_{2.5}Fe_{2.0}Ni_{5.5}Sb_5K_{0.2}O_{72.35}(SiO_2)_{60}$ was prepared as follows.

In 23 ml of water was dissolved 2.32 g of potassium nitrate, and the solution was added to 2067 g of a 20% silica sol. To the mixture was added a solution of 202.5 g of ammonium paramolybdate in 610 ml of water with stirring. Subsequently, a solution of 89.1 g of antimony tetroxide powder and 187.2 g of nickel nitrate in 190 ml of water, a solution of 94.6 g of iron nitrate in 95 ml of water, and a solution of 141.9 g of bismuth nitrate in 140 ml of 10% nitric acid were successively added to the mixture to prepare a slurry. To the slurry was added 40 g (corresponding to 5% of the oxide catalyst) of malic acid and dissolved therein. The resulting slurry had a pH of 1 or less. Then, the slurry was subjected to a heat treatment at 100° C. for 1 hour under refluxing and then the pH of the slurry was adjusted to a pH of 10 with 15% aqueous ammonia and 28% aqueous ammonia. The slurry was spray dried and calcined in the same manner as in Example 1.

EXAMPLES 11 AND 12

A catalyst having the same composition as in Example 10 was prepared in the same manner as in Example 10, except for replacing malic acid with 40 g (corresponding to 5% of the oxide catalyst) of oxalic acid o thioglycolic acid and adjusting the pH of the slurry after the heat treatment to a pH of 8.5 or 7.5, respectively.

EXAMPLE 13

A catalyst having the empirical formula $Mo_{10}Bi_{1.5}Fe_{1.5}Ni_{6.0}P_{1.0}K_{0.2}O_{43.1}(SiO_2)$ and weighing 800 g was prepared as follows.

In 25 ml of water was dissolved 2.68 g of potassium nitrate, and the solution was added to 2387 g of a 20% silica sol. To the mixture was added a solution of 233.8 g of ammonium paramolybdate in 700 ml of water with stirring. Then, a solution of 235.7 g of nickel nitrate in 235 ml of water, a solution of 81.9 g of iron nitrate in 80 ml of water, a solution of 98.3 g of bismuth nitrate in 100 ml of 10% nitric acid, and 15.3 g of a 85% phosphoric acid aqueous solution were successively added to the mixture to prepare a slurry. To the slurry was added 40 g (corresponding to 5% of the oxide catalyst) of glycine was added and dissolved therein. To the slurry were added 15% aqueous ammonia and 28% aqueous ammonia while stirring to adjust the pH of the slurry to a pH of 10. The slurry was heat treated at 100° C for 2 hours under refluxing and then adjusted to a pH of 1 with 10% nitric acid. The slurry was spray dried and calcined in the same manner as in Example 1.

EXAMPLES 14 AND 15

A catalyst having the same composition as in Example 13 was prepared in the same manner as in Example 13, except for replacing glycine with 40 g (corresponding to 5% of the oxide catalyst) of acetylacetone or phosphonopropane-1,2,3-tricarboxylic acid, adjusting the pH of the slurry before the heat treatment to a pH of 8 or 9.5, respectively, and adjusting the slurry after the heat treatment to a pH of 4 or 2, respectively.

EXAMPLES 16 TO 18

A catalyst having the composition shown in Table 1 below was prepared in the same manner as in Example 1. In the preparation, lead nitrate or telluric acid was used as a raw material for the lead component or the tellurium component, respectively, and it was added in the form of an aqueous solution subsequent to the addition of ammonium paramolybdate.

EXAMPLES 19 AND 20

A catalyst having the composition shown in Table 1 below was prepared in the same manner as in Example 8. In the preparation, chromium nitrate or cobalt nitrate was used as a raw material for the chromium component or the cobalt component, respectively, and it was added in the form of an aqueous solution subsequent to the addition of ammonium paramolybdate.

EXAMPLES 21 AND 22

A catalyst having the composition shown in Table 1 below was prepared in the same manner as in Example 11. In the preparation, cerium nitrate or ammonium paratungstate was used as a raw material for the cerium component or the tungsten component, respectively, and it was added in the form of an aqueous solution subsequent to the addition of ammonium paramolybdate.

EXAMPLES 23 TO 25

A catalyst having the composition shown in Table 1 below was prepared in the same manner as in Example 15. In the preparation, rubidium nitrate, cesium nitrate or orthoboric acid was used as a raw material for the rubidium component, the cesium component or the boron component, respectively. These components were each added in the form of an aqueous solution subsequently to the addition of ammonium paramolybdate.

Each of the catalysts prepared in Examples 1 to 25 was tested for catalytic activity and attrition resistance, and the results obtained are shown in Table 1 below.

TABLE 1

| Example No. | Mo | C Bi | Fe | Ni | D Sb | E P | F K | Si | Chelating Agent (wt %) | |
|---|---|---|---|---|---|---|---|---|---|---|
| 1 | 10 | 1.0 | 2.0 | 6.5 | 15 | 0.2 | 0.4 | 60 | Ethylenediamine | (5.0) |
| 2 | 10 | 1.0 | 2.0 | 6.5 | 15 | 0.2 | 0.4 | 60 | Triethanolamine | (5.0) |
| 3 | 10 | 1.0 | 2.0 | 6.5 | 15 | 0.2 | 0.4 | 60 | Ethylenediaminetetraacetic Acid | (5.0) |
| 4 | 10 | 1.5 | 2.0 | 6.0 | 10 | — | 0.2 | 60 | Tartaric Acid | (5.0) |
| 5 | 10 | 1.5 | 2.0 | 6.0 | 10 | — | 0.2 | 60 | Tartaric Acid | (2.5) |
| 6 | 10 | 1.5 | 2.0 | 6.0 | 10 | — | 0.2 | 60 | Tartaric Acid | (1.0) |
| 7 | 10 | 1.5 | 2.0 | 6.0 | 10 | — | 0.2 | 60 | Gluconic Acid | (5.0) |
| 8 | 10 | 1.5 | 2.0 | 6.0 | 10 | — | 0.2 | 60 | Citric Acid | (5.0) |
| 9 | 10 | 1.5 | 2.0 | 6.0 | 10 | — | 0.2 | 60 | Nitrilotriacetic Acid | (5.0) |
| 10 | 10 | 2.5 | 2.0 | 5.5 | 5 | — | 0.2 | 60 | Malic Acid | (5.0 |
| 11 | 10 | 2.5 | 2.0 | 5.5 | 5 | — | 0.2 | 60 | Oxalic Acid | (5.0) |
| 12 | 10 | 2.5 | 2.0 | 5.5 | 5 | — | 0.2 | 60 | Thioglycollic Acid | (5.0) |
| 13 | 10 | 1.5 | 1.5 | 6.0 | — | 1.0 | 0.2 | 60 | Glycine | (5.0) |
| 14 | 10 | 1.5 | 1.5 | 6.0 | — | 1.0 | 0.2 | 60 | Acetylacetone | (5.0) |
| 15 | 10 | 1.5 | 1.5 | 6.0 | — | 1.0 | 0.2 | 60 | Phosphonopropane-1,2,3-tricarboxylic Acid | (5.0) |
| 16 | 10 | 3.0 | 6.0 | — | — (Pb) | — | 0.4 | 60 | Ethylenediamine | (5.0) |
| 17 | 10 | 2.0 (Te) | — | — | 6.0 | — | 0.4 | 60 | Ethylenediamine | (5.0) |
| 18 | 10 | 1.0 | 2.0 | 6.5 | — (Cr) | — | 0.4 | 60 | Ethylenediamine | (5.0) |
| 19 | 10 | 0.5 | 1.5 | 6.0 | — | 1.0 (Co) | — | 0.4 | 60 Citric Acid | (5.0) |
| 20 | 10 | 2.0 | 2.0 | — | — | 6.5 (Ce) | — | 0.2 | 60 Citric Acid | (5.0) |
| 21 | 10 | 1.5 | 1.5 | 6.0 | 15 | 1.0 (W) | — | 0.5 | 40 Oxalic Acid | (5.0) |
| 22 | 10 | 1.0 | 1.0 | 6.5 | 15 | 0.5 | — | 0.2 (Rb) | 40 Oxalic Acid | (5.0) |
| 23 | 10 | 0.5 | 1.5 | 6.5 | 20 | — | — | 0.1 | 90 Phosphonopropane-1,2,3-tricarboxylic Acid | (5.0) |

TABLE 1-continued

| | | | | | | | (Cs) | | | | |
|---|---|---|---|---|---|---|---|---|---|---|---|
| 24 | 10 | 0.5 | 1.5 | 6.5 | 20 | — | — | 0.05 | 90 | Phosphonopropane-1,2,3-tricarboxylic Acid | (5.0) |
| | | | | | | | (B) | | | | |
| 25 | 10 | 1.0 | 1.0 | 6.5 | 10 | — | 0.5 | 1.0 | 90 | Phosphonopropane-1,2,3-tricarboxylic Acid | (5.0) |

| | Conditions of Slurry Preparation | | | | Calcination Temp. (°C.) | Reaction Conditions | | Reaction Results | | | |
|---|---|---|---|---|---|---|---|---|---|---|---|
| Example No. | pH | Heating Temp. (°C.) | Heating Time (hrs) | pH After Heating | | Temp. (°C.) | Contact Time (sec) | Acrylonitrile Yield (°C.) | Propylene Conversion (%) | Ammonia Combustion (%) | Attrition Loss (R value) |
| 1 | 8.0 | — | — | — | 620 | 410 | 4.0 | 86.1 | 98.7 | 16.0 | 1.2 |
| 2 | 6.0 | — | — | — | 620 | 410 | 4.0 | 85.6 | 98.5 | 17.0 | 1.5 |
| 3 | 10.0 | — | — | — | 620 | 410 | 4.0 | 86.2 | 99.0 | 15.5 | 1.4 |
| 4 | 8.0 | 100 | 2 | — | 620 | 410 | 4.0 | 85.8 | 98.5 | 13.0 | 1.3 |
| 5 | 8.0 | 100 | 2 | — | 620 | 410 | 4.0 | 85.5 | 98.6 | 16.0 | 1.0 |
| 6 | 8.0 | 100 | 2 | — | 620 | 410 | 4.0 | 85.3 | 98.7 | 16.5 | 1.5 |
| 7 | 6.0 | 100 | 2 | — | 620 | 410 | 4.0 | 85.9 | 98.6 | 16.0 | 1.0 |
| 8 | 9.5 | 100 | 2 | — | 620 | 410 | 4.0 | 86.1 | 98.6 | 14.5 | 1.0 |
| 9 | 11.0 | 100 | 2 | — | 620 | 410 | 4.0 | 85.7 | 98.5 | 15.0 | 0.9 |
| 10 | — | 100 | 1 | 10.0 | 600 | 410 | 4.0 | 85.2 | 98.7 | 16.0 | 1.3 |
| 11 | — | 100 | 1 | 8.5 | 600 | 410 | 4.0 | 85.4 | 98.9 | 16.1 | 1.4 |
| 12 | — | 100 | 1 | 7.5 | 600 | 410 | 4.0 | 85.3 | 98.4 | 15.5 | 1.6 |
| 13 | 10.0 | 100 | 2 | 1.0 | 580 | 410 | 4.0 | 84.3 | 98.8 | 16.5 | 0.9 |
| 14 | 8.0 | 100 | 2 | 4.0 | 580 | 410 | 4.0 | 84.7 | 99.0 | 15.5 | 1.0 |
| 15 | 9.5 | 100 | 2 | 2.0 | 580 | 410 | 4.0 | 84.5 | 98.7 | 16.0 | 0.8 |
| 16 | 8.0 | — | — | — | 600 | 430 | 4.5 | 78.5 | 98.8 | 15.5 | 1.5 |
| 17 | 8.0 | — | — | — | 600 | 470 | 4.5 | 81.6 | 98.5 | 13.2 | 1.8 |
| 18 | 8.0 | — | — | — | 550 | 410 | 4.5 | 75.5 | 96.2 | 15.7 | 1.7 |
| 19 | 9.5 | 100 | 2 | — | 600 | 410 | 4.0 | 84.5 | 98.7 | 15.5 | 1.4 |
| 20 | 9.5 | 100 | 2 | — | 550 | 410 | 4.5 | 84.3 | 98.8 | 16.0 | 1.3 |
| 21 | — | 100 | 1 | 8.5 | 600 | 410 | 3.5 | 84.7 | 98.5 | 14.0 | 1.7 |
| 22 | — | 100 | 1 | 8.5 | 620 | 410 | 3.5 | 86.2 | 99.0 | 13.5 | 1.8 |
| 23 | 9.5 | 100 | 2 | 2.0 | 600 | 410 | 5.5 | 85.1 | 98.9 | 14.5 | 1.7 |
| 24 | 9.5 | 100 | 2 | 2.0 | 600 | 410 | 5.5 | 85.0 | 98.5 | 14.5 | 1.8 |
| 25 | 9.5 | 100 | 2 | 2.0 | 600 | 410 | 5.5 | 84.8 | 98.8 | 14.7 | 1.6 |

COMPARATIVE EXAMPLES 1 TO 4

A catalyst having a composition corresponding to Examples 1, 8, 10, and 13 was prepared in accordance with the respective preparation method, except for using no chelating agent.

Each of the resulting catalysts was tested for catalytic activity and attrition resistance, and the results obtained are shown in Table 2 below. As is apparent from the results of Table 2, these comparative catalysts containing no chelating agent give lower attrition resistance.

COMPARATIVE EXAMPLE 5

A catalyst having the same composition as in Example 1 was prepared in the same manner as in Example 1, except for adjusting the pH of the slurry to a pH of 5 with 15% aqueous ammonia.

COMPARATIVE EXAMPLE 6

A catalyst having the same composition as in Example 4 was prepared in the same manner as in Example 4, except for adjusting the pH of the slurry before and after the heat treatment to a pH of 0.2 with 10% nitric acid.

Each of the comparative catalysts prepared in Comparative Examples 5 and 6 was tested for catalytic activity and attrition resistance, and the results obtained are shown in Table 2 below.

COMPARATIVE EXAMPLES 7 TO 9

A catalyst corresponding to the catalyst of Example 16, 17 and 18 was prepared according to the respective process, except that ethylenediamine was not added.

COMPARATIVE EXAMPLE 10

A catalyst having the same composition as in Example 20 was prepared in the same manner as in Example 20, except that no citric acid was used.

Each of the comparative catalysts prepared in Comparative Examples 7 to 10 was tested for catalytic activity and attrition resistance, and the results obtained are shown in Table 2 below.

TABLE 2

| Comparative Example No. | Composition (atomic ratio) | | | | | | | | Chelating Agent (wt %) | |
|---|---|---|---|---|---|---|---|---|---|---|
| | Mo | C | | D | | E | F | | | |
| | | Bi | Fe | Ni | Sb | | P | K | Si | |
| 1 | 10 | 1.0 | 2.0 | 6.5 | 15 | — | 0.2 | 0.4 | 60 | — — |
| 2 | 10 | 1.5 | 2.0 | 6.0 | 10 | — | — | 0.2 | 60 | — — |
| 3 | 10 | 2.5 | 2.0 | 5.5 | 5 | — | — | 0.2 | 60 | — — |
| 4 | 10 | 1.5 | 1.5 | 6.0 | — | — | 1.0 | 0.2 | 60 | — — |
| 5 | 10 | 1.0 | 2.0 | 6.5 | 15 | — | 0.2 | 0.4 | 60 | Ethylenediamine (5.0) |
| 6 | 10 | 1.5 | 2.0 | 6.0 | 10 | — | — | 0.2 | 60 | Tartaric Acid (5.0) |
| 7 | 10 | 3.0 | 6.0 | — | — | (Pb) — | — | 0.4 | 60 | — — |
| 8 | 10 | 2.0 (Te) | — | — | — | 6.0 | — | 0.4 | 60 | — — |
| 9 | 10 | 1.0 | 2.0 | 6.5 | — | (Co) — | — | 0.4 | 60 | — — |

TABLE 2-continued

| | | Conditions of Slurry Preparation | | | Calcination Temp. (°C.) | Reaction Conditions | | Reaction Results | | | |
|---|---|---|---|---|---|---|---|---|---|---|---|
| Example No. | pH | Heating Temp. (°C.) | Heating Time (hrs) | pH After Heating | | Temp. (°C.) | Contact Time (sec) | Acrylonitrile Yield (°C.) | Propylene Conversion (%) | Ammonia Combustion (%) | Attrition Loss (R value) |
| 10 | 10 | 2.0 | 2.0 | — — | 6.5 | — | 0.2 | 60 | — | | — |
| 1 | 8.0 | — | — | — | 620 | 410 | 4.0 | 85.2 | 98.7 | 16.2 | 5.1 |
| 2 | 9.5 | 100 | 2 | — | 620 | 410 | 4.0 | 85.9 | 99.3 | 13.5 | 7.4 |
| 3 | — | 100 | 1 | 10.0 | 620 | 410 | 4.0 | 85.0 | 99.1 | 15.4 | 5.0 |
| 4 | 10.0 | 100 | 2 | 1.0 | 620 | 410 | 4.0 | 84.5 | 99.0 | 16.5 | 3.5 |
| 5 | 5.0 | — | — | — | 620 | 410 | 4.5 | 83.5 | 99.0 | 22.5 | 1.9 |
| 6 | 0.2 | 100 | 1 | 0.2 | 620 | 410 | 4.5 | 82.7 | 98.7 | 25.3 | 1.0 |
| 7 | 8.0 | — | — | — | 600 | 430 | 4.5 | 78.3 | 99.0 | 15.6 | 4.0 |
| 8 | 8.0 | — | — | — | 600 | 470 | 4.5 | 81.5 | 98.3 | 13.5 | 5.5 |
| 9 | 8.0 | — | — | — | 550 | 410 | 4.5 | 75.0 | 96.0 | 16.0 | 6.2 |
| 10 | 9.5 | 100 | 2 | 9.5 | 550 | 410 | 5.0 | 84.0 | 98.6 | 16.3 | 5.7 |

It can be seen from the results of Table 2 that the comparative catalysts prepared at a low pH achieve only a low acrylonitrile yield and a high ammonia combustion.

While the invention has been described in detail and with reference to specific embodiments thereof, it will be apparent to one skilled in the art that various changes and modifications can be made therein without departing from the spirit and scope thereof.

What is claimed is:

1. A process for producing a molybdenum-containing metal oxide fluid-bed catalyst comprising, as essential components,
   (i) at least one element selected from the group consisting of iron, bismuth, and tellurium,
   (ii) molybdenum, and
   (iii) silica,
   which comprises (a) adjusting an aqueous slurry containing a raw material providing element (i), a molybdenum compound, a silica sol, and a chelating agent capable of inhibiting gelation of the slurry to a pH of at least 6, or (b) adjusting an aqueous slurry containing a raw material providing element (i), a molybdenum compound and a chelating agent capable of inhibiting gelation to a pH of at least 6 and mixing the slurry with a silica sol,
   then spray drying the thus pH-adjusted aqueous slurry, and
   calcining the resulting particles.

2. A process as claimed in claim 1, wherein said process comprises subjecting the aqueous slurry containing silica to a heat treatment at a temperature of from 50 to 120° C. for at least 10 minutes while maintaining the form of a slurry prior to the spray drying.

3. A process as claimed in claim 1, wherein the resulting catalyst is represented by the empirical formula:

$$Mo_aC_cD_dE_eF_fO_g(SiO_2)_h$$

wherein
C represents at least one element selected from the group consisting of Fe, Bi, and Te;
D represents at least one element selected from the group consisting of Ni, Co, Mg, Cr, Mn, Cu, Zn, Ga, Ge, Cd, In, Sn, Sb, V, W, Re, Pb, Ru, Rh, Pd, Os, Ir, Pt, Th, U, La, Ce, Pr, Nd, Sm, Eu, Gd, Al, Ti Ta, Nb, and Zr;
E represents at least one element selected from the group consisting of P and B;
F represents at least one element selected from the group consisting of Li, Na, K, Rb, Cs, Ca, Sr, Ba, and Tl;
O is oxygen; and
a, b, c, d, e, f, g, and h each represents the atomic ratio of elements for which they are subscripts and, wherein when a = 8 to 12,
c = 0.5 to 20,
d = 0 to 25,
e = 0 to 5,
f = 0 to 5,
g is a number determined by a, b, c, d, e, and f so as to form an oxide of the corresponding elements, and
h = 20 to 150.

4. A process as claimed in claim 2, wherein the resulting catalyst is represented by empirical formula:

$$Mo_aC_cD_dE_eF_fO_g(SiO_2)_h$$

wherein
C represents at least one element selected from the group consisting of Fe, Bi, and Te;
D represents at least one element selected from the group consisting of Ni, Co, Mg, Cr, Mn, Cu, Zn, Ga, Ge, Cd, In, Sn, Sb, V, W, Re, Pb, Ru, Rh, Pd, Os, Ir, Pt, Th, U, La, Ce, Pr, Nd, Sm, Eu, Gd, Al, Ti, Ta, Nb, and Zr;
E represents at least one element selected from the group consisting of P and B;
F represents at least one element selected from the group consisting of Li, Na, K, Rb, Cs, Ca, Sr, Ba, and Tl;
O is oxygen; and
a, b, c, d, e, f, g, and h each represents the atomic ratio of elements for which they are subscripts and, wherein when a = 8 to 12,
c = 0.5 to 20,
d = 0 to 25,
e = 0 to 5,
f = 0 to 5,
g is a number determined by a, b, c, d, e, and f so as to form an oxide of the corresponding elements, and
h = 20 to 150.

5. A process as claimed in claim 1, wherein said chelating agent is at least one compound selected from the group consisting of an amine, an aminopolycarboxylic acid, a polycarboxylic acid, an aromatic carboxylic acid, a hydroxycarboxylic acid, a keto-carboxylic acid, a thiol, a sulfur compound, an amino acid, a diketone, and a phosphonic acid.

6. A process as claimed in claim 2, wherein said chelating agent is at least one compound selected from the group consisting of an amine, an aminopolycarboxylic acid, a polycarboxylic acid, an aromatic carboxylic acid, a hydroxycarboxylic acid, a keto-carboxylic acid, a thiol, a sulfur compound, an amino acid, a diketone, and a phosphonic acid.

7. A process as claimed in claim 1, wherein said process comprises adjusting the pH of the aqueous slurry to a pH of from 6 to 11.

8. A process as claimed in claim 1, wherein said catalyst is a catalyst for ammoxidation.

* * * * *